United States Patent [19]

Setterquist

[11] 4,017,525

[45] Apr. 12, 1977

[54] TETRA(NEOPHYL) ZIRCONIUM

[75] Inventor: Robert Alton Setterquist, Wilmington, Del.

[73] Assignee: E. I. DuPont de Nemours and Company, Wilmington, Del.

[22] Filed: July 30, 1975

[21] Appl. No.: 600,296

Related U.S. Application Data

[62] Division of Ser. No. 471,813, May 20, 1975, Pat. No. 3,932,307.

[52] U.S. Cl. .......................... 260/429.3; 252/430; 252/431 R; 526/170
[51] Int. Cl.$^2$ .......................................... C07F 7/00
[58] Field of Search .............................. 260/429.3

[56] References Cited

UNITED STATES PATENTS 3,763,197  10/1973  Collier et al. ................ 260/429.3
3,813,423  5/1974  Pioli et al. ..................... 260/429.3

OTHER PUBLICATIONS

Chem. Abstracts, vol. 64, 14212e (1966).
Chem. Abstracts, vol. 64, 5131g (1966).

*Primary Examiner*—Helen M. S. Sneed

[57] ABSTRACT

There are disclosed olefin polymerization catalysts based on tetra(neophyl) zirconium and its reaction products with surface-hydroxylated oxides of metals of Groups II($a$), III($a$), IV($a$) and IV($b$) of the Periodic Table of the Elements, processes for their preparation, and processes for the polymerization of olefinic monomers employing such catalysts. Neophyl zirconium aluminate supported on alumina is disclosed as the preferred, most active catalyst. The polyolefins produced are linear high polymers of high crystallinity such as polyethylene and isotactic polypropylene. Diolefins are converted into rubber by use of the process employing the catalyst. Ethylene-propylene copolymer rubbers can also be produced by use of the catalysts.

1 Claim, 3 Drawing Figures

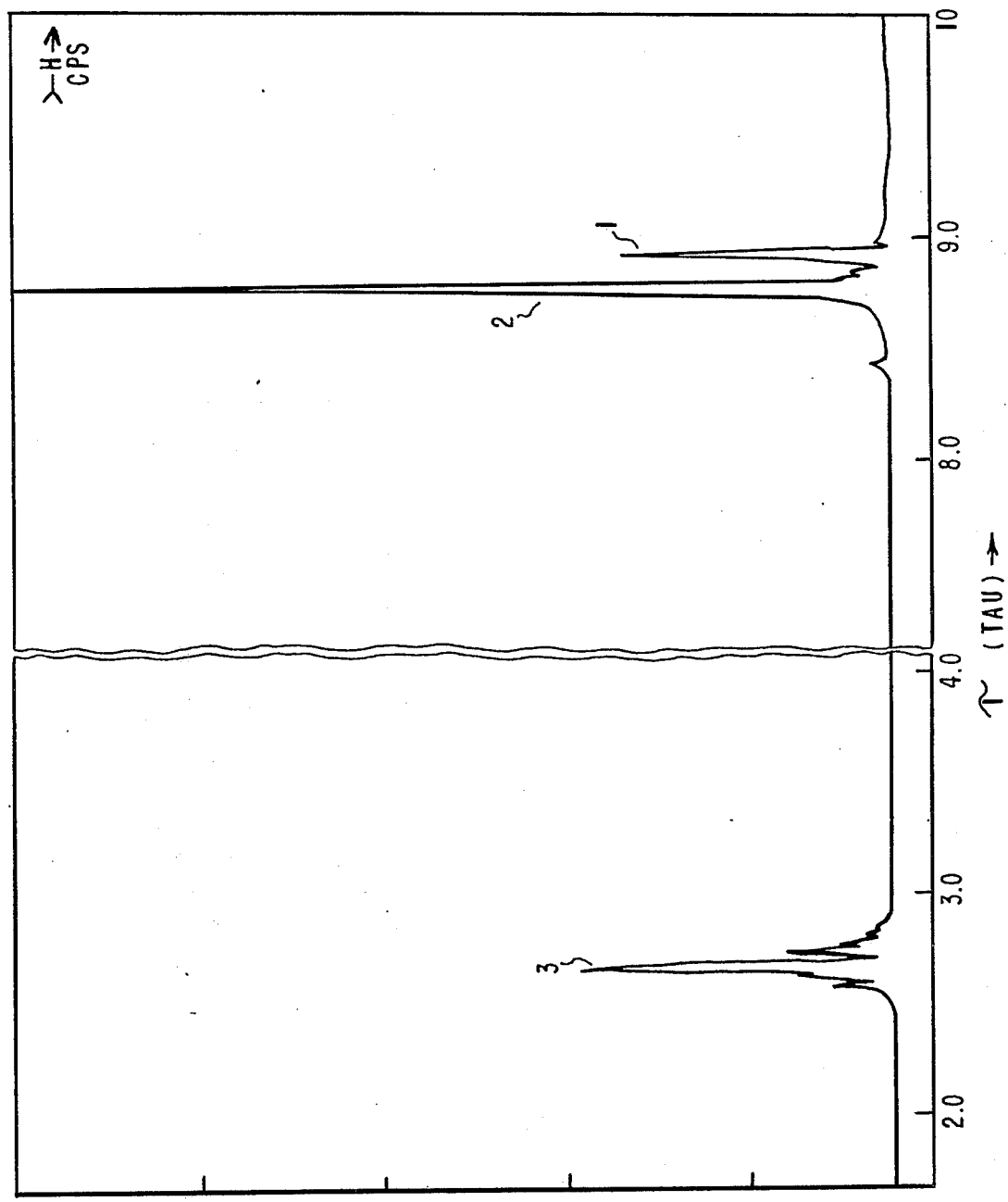
FIG. IIA

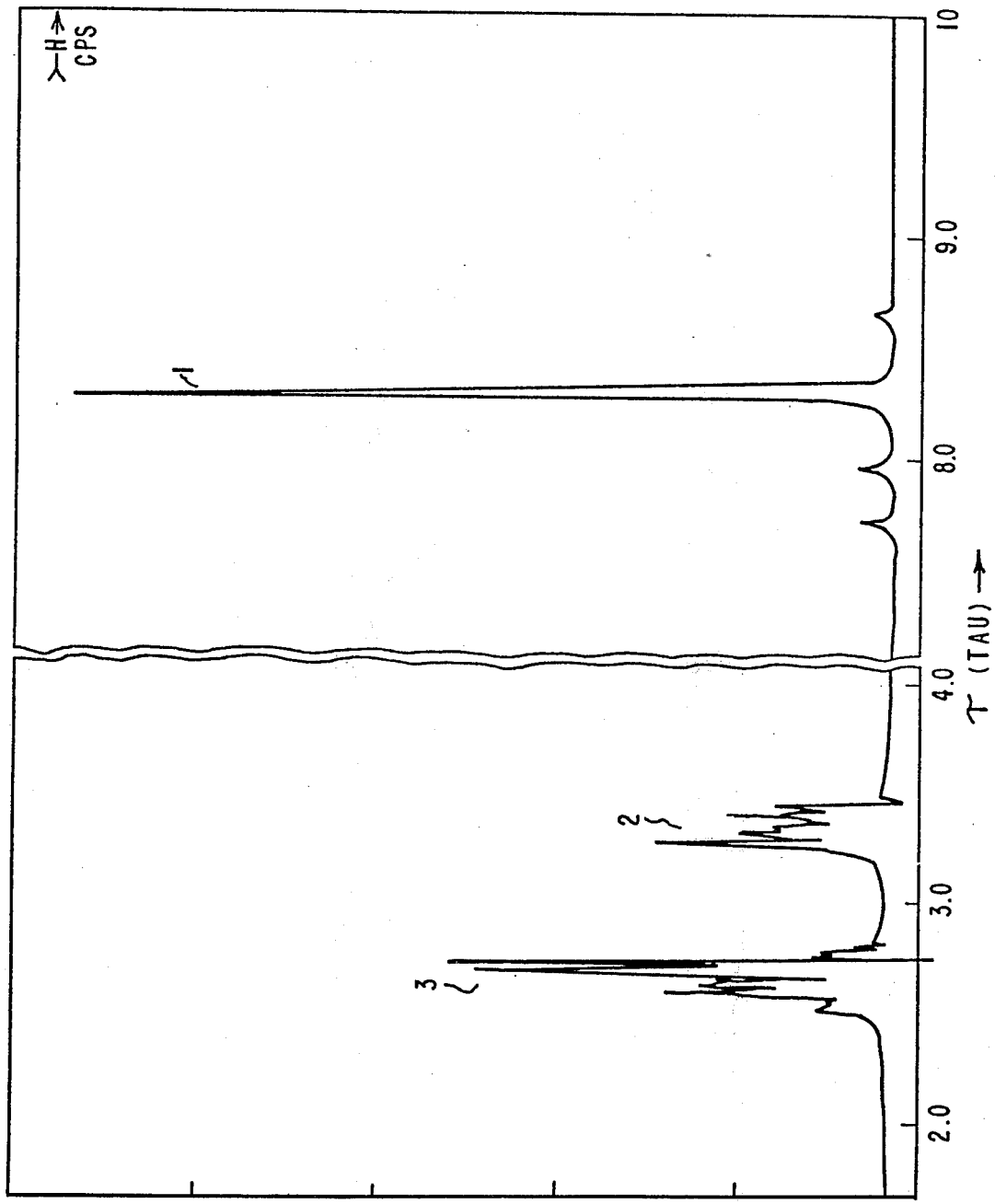
FIG.IIB

TETRA(NEOPHYL) ZIRCONIUM

This is a division of application Ser. No. 471,813, filed May 20, 1975, now U.S. Pat. No. 3,932,307.

BACKGROUND OF THE INVENTION

1. Field of the Invention

This invention relates to an improved process for the polymerization of olefins to provide linear polymers and copolymers, said process employing an improved catalyst comprising tetra(neophyl) zirconium, or its reaction products with metal oxides, for use therein. More specifically, this invention relates to a process for the homopolymerization and copolymerization of ethylene, propylene, butene-1 and higher 1-olefins in which the catalyst is either tetra(neophyl) zirconium or, preferably, the product obtained by the reaction of tetra(neophyl) zirconium with a partially hydrated metal oxide surface. The metal oxide can be an oxide selected from a metal of Groups II(a), III(a), IV(a), or IV(b) of the Bohr Periodic Table of the Elements such as fumed $Al_2O_3$, fumed $TiO_2$, fumed $SiO_2$, MgO, coprecipitated $Al_2O_3 \cdot ZrO_2$ or $SiO_2 \cdot Al_2O_3$ in each case free from merely absorbed $H_2O$ but partially surface-hydrated. The most active, preferred catalyst is neophyl zirconium aluminate or alumina prepared from the reaction of tetra(neophyl) zirconium with fumed $Al_2O_3$ having 0.5 to 1.5% water of hydration on its surfaces prior to reaction with tetra(neophyl) zirconium.

2. Prior Art

In 1954 and 1955 pioneering advances in olefin polymerization catalysts were disclosed by Karl Ziegler and associates at the Max-Planck Institute for Coal Research in Mulheim, Germany, and by Arthur Anderson and associates in the laboratories of E. I. du Pont de Nemours and Company in Wilmington, Delaware. These new catalyst systems, now frequently termed coordination catalysts, were based on transition metal salts (e.g. titanium, zirconium or vanadium halides) which had been converted into reduced valence states by reaction with a variety of alkylating or arylating substances, usually simple organometallic compounds of a metal of Groups I, II or III of the Periodic Table of Elements. It is believed that the mechanism of catalyst production involves alkylation (or arylation) of the transition metal halide followed by rapid decomposition of the unstable, transitory transition metal-alkyl (or aryl) compounds to give more stable complex products of lower valency which actively coordinate with and polymerize olefins by a coordination-polymerization mechanism. Unlike the commercial polyethylene or any polypropylene previously known prepared by free-radical or ionic catlysts, polyolefins prepared with coordination catalysts are of very high molecular weight and linear and highly ordered, thus exhibiting, in the case of homopolymers, such a high degree of chemical structural regularity and linearity that they are highly crystalline and exhibit high crystalline melting points, making them extremely valuable as textile fibers films, and molded articles of commerce. Generally, however, it has been necessary in the case of these coordination catalysts to devise processes to remove the catalyst residues, which comprised the transition metal halides, since the residues were present at such levels as to discolor the polymer and the halide was too corrosive in subsequent fabrication machinery.

More recently some more stable organometallic transition metal complexes, usually including a halide anionic ligand or a neutral Lewis Base ligand, have been disclosed in patents of Günther Wilke of the Max-Planck Institute and by patents of several researchers in the laboratories of I.C.I. in England.

Illustrative of the Wilke patents are U.S. Pat. Nos. 3,379,706, 3,424,777, 3,432,530, 3,540,728, 3,468,921, and 3,536,740. In all of these Wilke patents the hydrocarbyl groups attached to a transition metal are members of the class of π-allylic compounds characterized by the structure

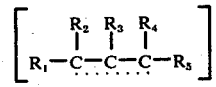

in which the R-radicals may be H- or any alkyl, aryl or alkaryl radicals of $R_1$ and $R_4$ may together form a ring comprising methylene groups. Interactions between the π electrons and the electrons of the transition metal presumably occur affecting the stability and chemical reactivity of the complexes. These metal-π-allyl compounds are reacted with Lewis acids, such as HX, where X is halide, or Lewis Bases, such as tertiary amines or phosphines, to form complexes showing activity as olefin oligomerization or polymerization catalysts. However, polymerization reactions using such catalysts generally must be conducted as slurry polymerizations at low temperatures, because of marginal thermal stability and low solubility of the π allyl complexes, and have been found less that fully satisfactory in the yields and molecular weight of polymers produced. Furthermore, because of their corrosive and often toxic nature, the catalyst residues must be removed from the polymeric products by time-consuming and costly procedures in order to provide products of general utility and safety in commerce.

One improvement on the use of these π-allylic transition metal complex catalysts in olefin polymerization is disclosed in U.S. Pat. No. 3,732,198 of Whitely et al., assignors to I.C.I., who disclose the polymerization of ethylene with a combination of a classical coordination catalyst with a transition metal complex of a π-allylic compound.

The patents arising from the work of researchers at I.C.I. in England are illustrated by U.S. Pat. Nos. 3,681,317, 3,740,384, 3,738,944 and British Patent 1,314,828. All of these involve tetra(benzyl)-transition metal compounds (e.g. tetra(benzyl) zirconium) complexed with anionic ligands (e.g. halide) and/or neutral ligands (e.g. pyridine) as ethylene polymerization catalysts. In certain cases there are disclosed as ethylene polymerization catalysts the reaction products of tetra(benzyl)-zirconium compounds with inorganic oxides free of absorbed water by containing surface HO— groups. Reasonable thermal stability is achieved with these substances. They apparently yield high molecular weight polyethylene but the polymerization rate and efficiency and polymer yield obtained with those catalysts in processes for the polymerization of ethylene are generally not as good as with classical coordination catalysts, and hence again it would be necessary to remove catalyst residues in order to produce polyethylene suitable for general fabrication techniques.

OBJECTS OF THE INVENTION

An object of this invention is to provide an improved process for the polymerization and copolymerization of ethylene and other 1-olefins (particularly propylene, butene-1, pentene-1, hexene-1, heptene-1, octene-1, nonene-1 and decene-1), as well as diolefins, to linear, regular, head-to-tail polymers of high molecular weight in which exceptionally high rates of polymerization and yields of polymer are achieved using halogen-free catalysts.

Another object of this invention is to provide improved olefin polymerization catalysts of substantially greater activity than previously known and having substantial thermal stability.

Another object of this invention is to provide a solution, single phase process for the polymerization of ethylene and other 1-olefins at elevated temperatures in which such high polymerization rates and catalyst efficiencies are achieved that catalyst residues need not be removed from the resultant polymers because of their low concentration, non-corrosive properties and non-toxic nature.

Another object of this invention is to provide an integrated process for the activation of an olefin polymerization catalyst to the optimum extent for use by injection into an olefin polymerization zone maintained at a preselected temperature.

Other objects and advantages of the invention will be apparent from the description and examples which follow.

SUMMARY OF THE INVENTION

It has been discovered that the objects of this invention are attained by employing, as catalyst in a process for the polymerization of the olefins in hydrocarbon medium, a solution in inert hydrocarbon solvent of tetra(neophyl) zirconium or, preferably, a suspension of a metal oxide of a metal of Groups II($a$), III($a$), IV($a$) or IV($b$), preferably alumina, having chemically bonded onto its surfaces neophyl zirconium metallate prepared, prior to contacting with an olefin monomer, by reacting a hydrocarbon solution of a tetra(neophyl) zirconium with a suspension in hydrocarbon medium of a surface hydrated metal oxide free from any merely absorbed $H_2O$. Representative examples of suitable oxides are $Al_2O_3$, $TiO_2$, $SiO_2$, MgO, coprecipitated $Al_2O_3 \cdot ZrO_2$ and coprecipitated $SiO_2 \cdot Al_2O_3$, in each case having a surface area in the range of 10–500 m²/g, as measured by $N_2$ adsorption. Preferred and especially active metal oxide supports have been prepared from fumed aluminas, such as those sold by Degussa ("Almunia C") and Cabot Corporation ("Alon G").

It has further been discovered that in order to obtain the most active catalyst of this invention, it is preferred to modify the crystalline form of the alumina and control the extent of hydration on its surfaces prior to reaction with tetra(neophyl) zirconium by activating the alumina by heat treatment under a flow of an inert anhydrous gas (e.g. $N_2$) at a temperature in the range of 900° to 1100° C. for 1 to 10 hours followed by hydration to the extent of 3% to 5% by contract with an atmosphere containing water vapor followed by dehydration by heating at 300° to 500° C. for 1 to 10 hours to provide an alumina containing 0.5% to 1.5% water as HO- groups on the surfaces of the alumina. The preferred catalyst, neophyl zirconium aluminate, bonded onto the surfaces of the alumina, is then prepared either by contacting a suspension of the hydrated alumina in anhydrous inert hydrocarbon medium with from 0.05 to 0.6, preferably 0.15 to 0.35, millimoles of tetra(neophyl) zirconium, dissolved in any anhydrous inert hydrocarbon solvent, per gram of suspended $Al_2O_3$ at 0° to 100 ° C until the reaction is complete.

It has been found that the reaction product of tetra (neophyl) zirconium with a hydrated metal oxide tends to undergo spontaneous transformation, particularly at temperatures of 50° to 100° C. and above, to thermally stable, lower valence states in which the zirconium is present at least in part at a valence of three. However, such prior reduction is not necessary if the catalyst is to be employed in polymerization processes conducted at temperatures above 100° C.

The polymerization of olefins with the catalysts of this invention can be conducted at temperatures in the range of 10° to 300° C. at pressures varying, with temperature, from atmospheric to 1000 atmospheres of above, the pressure being selected high enough to keep the monomers in solution. For ethylene polymerization of a slurry type, temperatures in the range of 10° to 110° C. are suitable. For the solution polymerization of ethylene, which is preferred, temperatures can range from 125° C. to 300 ° C. but preferred temperatures are in the range of 130° to 270° C. Any inert hydrocarbon can be employed as a polymerization medium. Suitable classes include n-alkanes, cycloalkanes and aromatic hydrocarbons, representative examples being propane, n-hexane, cyclohexane, n-heptane, and toluene. Hydrogen can be added to the polymerization zone to control and limit the molecular weight of the polyolefin produced.

DESCRIPTION OF THE DRAWINGS

FIG. I is a schematic drawing of the continuous process of this invention in which a solution of the tetra (neophyl) zirconium from feed tank, 6, and of the slurry of alumina in inert hydrocarbon from feed tank, 7, are passed, through mixing valve, 15, to premix vessel, 1, agitated by mixer, 12. After a preselected hold-up time in the premix vessel, the slurry is passed to reaction vessel, 2, where the slurry is heated to complete the reaction while being stirred by mixer, 13. After a preselected hold-up time in the reaction vessel, the slurry of neophyl zirconium aluminate supported on alumina is passed out through valve 16 to a polymerization vessel, 3, which is thoroughly mixed by mixer, 14, to provide a uniform, constant environment. Ethylene, or other olefin feed, from reservoir, 9, is passed through mixing valve 17, where it is admixed with recycling polymerization medium from polymer separator, 5, and then fed into polymerizer, 3. After a preselected hold-up time in the polymerization vessel, the reaction mixture is passed through mixing valve, 19, where catalyst deactivator from reservoir, 10, is added and the mixture passed through a tubular, turbulent mixer, 4, and, through pressure let-down valve, 20, to the polymer separator, 5. From the separator, polymer stream is passed to polymer recovery system, 11, while the liquid polymerization medium is passed back as recycle to the polymerizer, 3.

The catalyst deactivator from reservoir 10 can be an alcohol, steam, $CO_2$ or other polar composition reactive with the transition metal catalyst. The traces of deactivated catalyst are removed from the polymer separator incorporated with the polymer from which they need not be removed because of the low level and inert nature of this innocuous catalyst residue.

Figure 1:
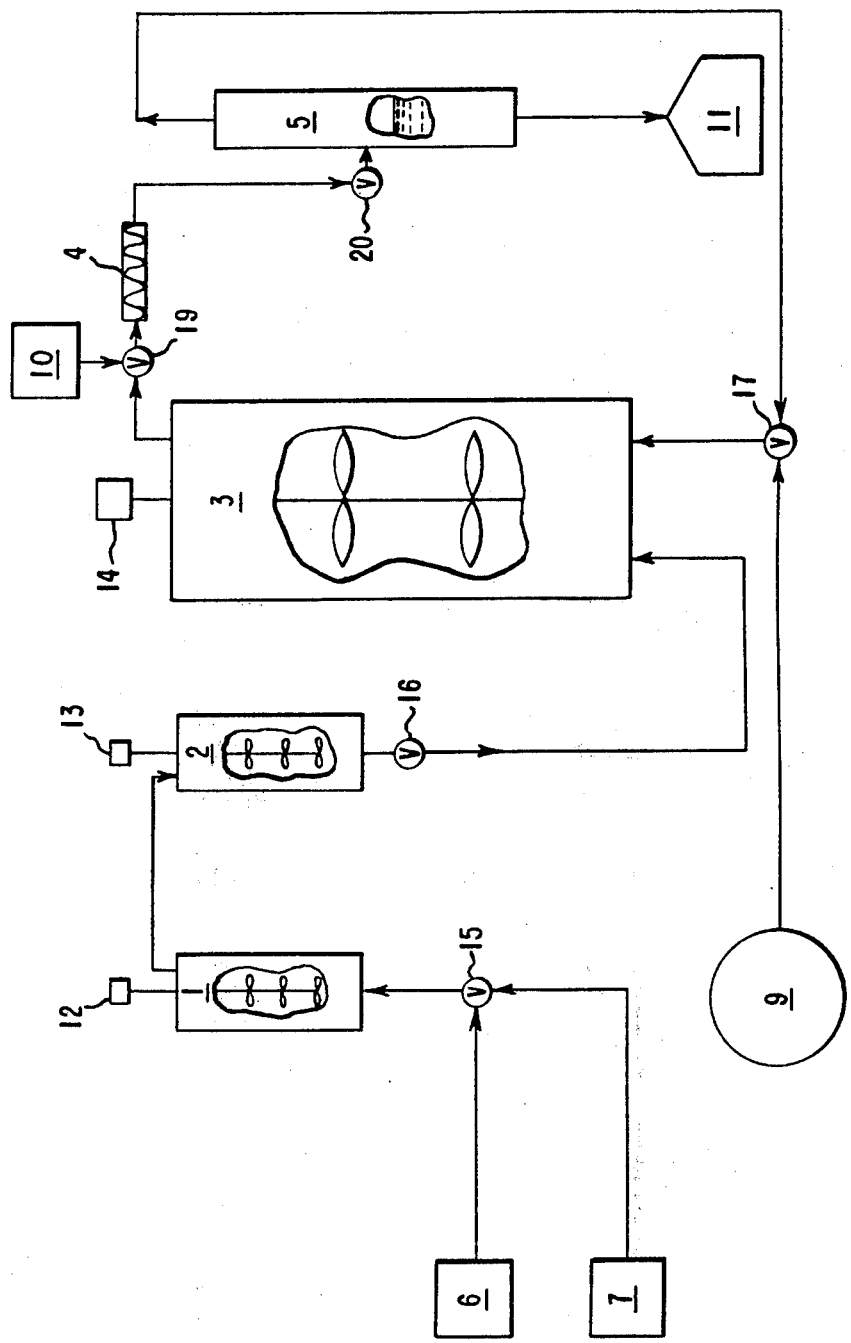

FIG. II-A shows the nuclear magnetic resonance spectrum (60MC) of tetra(neophyl) zirconium. On FIG. II-A, the absorption peak due to the methylene protons is indicated at (1) that due to the methyl protons at (2), and that due to protons on the aromatic ring at (3); these protons can be identified by reference to the chemical formula:

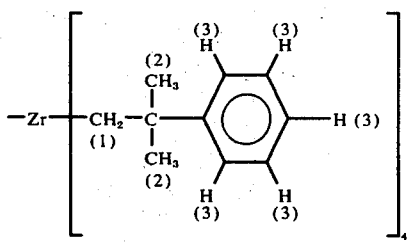

In FIG. II-B there is shown for comparison the NMR spectrum obtained in the same manner, of tetra(benzyl) zirconium:

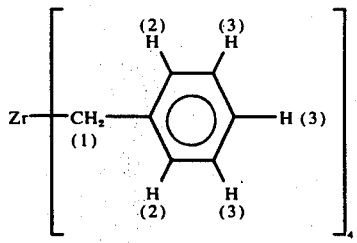

on FIG. II-B the absorption due to the methylene protons is again shown at (1); there are, of course, no methyl protons, but two bands for the protons on the aromatic ring are seen at (2) and (3) corresponding to protons at positions indicated by (2) and (3) on the above formula.

DESCRIPTION OF PREFERRED EMBODIMENTS

Tetra(neophyl) zirconium, otherwise identified as tetra kis(2-methyl, 2-phenylpropyl) zirconium, can be prepared by the reaction of a zirconium tetrahalide, preferably $ZrCl_4$, with an organometallic compound of a metal of Groups I, II, or III of the Periodic Table of the Elements according to Bohr (see T. Moeller, "Inorganic Chemistry," p. 122) in which the organic radicals attached to the metal are neophyl radicals. A convenient method of preparation is the reaction of an ethereal solution of the neophyl Grignard reagent with $ZrCl_4$ according to the following reaction:

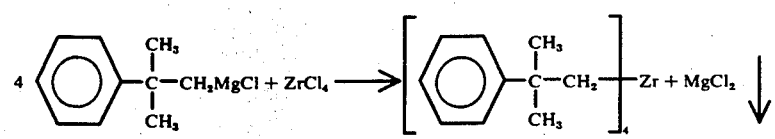

The reaction of the Grignard reagent with the $ZrCl_4$ is most conveniently carried out in an anhydrous liquid medium by adding powdered $ZrCl_4$ as a solid or slurry in an inert anhydrous liquid to a solution of the neophyl Grignard reagent. The temperature in the reaction vessel should be maintained in the range of 0° to 70° C. Maintenance of dry, oxygen-free conditions during the addition and reaction is essential. An ethyl ether-toluene mixed solvent is suitable as the medium. The resultant tetra(neophyl) zirconium is soluble in hydrocarbon solvents or ether-hydrocarbon mixed solvents, and the solution is readily separated from the precipitated $MgCl_2$ by decantation or filtration. Pure crystalline tetra(neophyl) zirconium can be recovered by evaporation of the solvent followed by recrystallization from a hydrocarbon solvent such as toluene by warming, cooling and filtration. The resultant purified crystals are cream to light tan in color and melt at 67°–68° C. (hot stage) or 69° C. (DSC method). The crystalline tetra(neophyl) zirconium is thermally stable and can be stored without decomposition at 25° C. for many hours or at −35° C. for many weeks. Thermolysis studies shownned that very little decomposition, as measured by weight loss, occurred when tetra(neophyl) zirconium was heated at 10° C./min. until after temperatures above 100° C. were reached. This thermal stability was unexpected in view of the known instability of many other tetra(hydrocarbyl) zirconium compounds such as tetra(alkyl) zirconiums. Thermal decomposition of tetra(neophyl) zirconium at temperatures above 100° C. yields primarily t-butyl benzene and a dark residue readily oxidized to a white zirconium oxide by air.

The unique structure of tetra(neophyl) zirconium is also revealed by its nuclear magnetic resonance spectrum (NMR) FIG. II-A, which shows methylene protons at 8.93 τ, methyl protons at 8.76 τ and phenyl portons at 2.7 τ. Since the NMR spectrum of tetra(neophyl) zirconium shows no broadening of the peak due to the phenyl protons, it appears that no interaction between the π-electrons of the benzene ring and the d-orbitals of zirconium occurs in this compound distinguishing it from the π-allyl and benzyl zirconium compounds of the prior art which show such interaction (see FIG. II-B). The absence of such interaction changes the chemical reactivity of the zirconium-hydrocarbon bond. Also, the greater stability of tetra(neophyl) zirconium, compared to many other tetra(hydrocarbyl) zirconium compounds (e.g. tetra(alkyl) zirconium) must be associated with the absence of a hydrogen atom on the carbon beta to the metal; this reduces the tendency for decomposition via β-hydride transfer an olefin elimination.

Rather surprisingly, tetra(neophyl) zirconium alone has been found to be an effective catalyst for the polymerization of ethylene and other α-olefins to yield high molecular weight, solid, linear polyolefins. While not wishing to be bound by any particular theory of the mechanism, it is believed probable that, upon contact of the tetra(neophyl) zirconium with a polymerizable olefin under polymerization conditions, a metathesis occurs whereby one or more neophyl radicals are replaced by the aliphatic radicals corresponding to the olefin to be polymerized, and, thereupon, there occurs a partial decomposition due to the known instability of Zr-aliphatic bonds so that the zirconium is then reduced in valence to the lower-valence forms (ZrII and ZrIII) known to be active as coordination catalysts in the polymerization of olefins.

Even more active catalysts for the polymerization of olefins are obtained by reacting tetra(neophyl) zirconium with a hydrated metal oxide of the classes previously defined. In the course of this reaction, particularly as the temperature of the reactants is raised, the zirconium-metal oxide reaction product undergoes partial decomposition to provide neophyl zirconium in the active, lower valence states, chemically bonded to the surfaces of the metal oxide which can then be dispersed in an inert hydrocarbon and passed to a polymerization zone where the catalyst contacts the olefin monomer and converts it to a high molecular weight, solid, linear polyolefin. If desired, these supported zirconium neophyl metal oxide catalysts can also be used as fluidized beds to polymerize gaseous olefins to high molecular weight polyolefins.

The preferred catalyst, in a process for the polymerization of ethylene and/or other 1-olefins, is, however, meophyl zirconium aluminate supported on and bonded to fumed alumina having a surface area in the range of 10 to 500 m$^2$/g, as measured by N$_2$ adsorption. Prior to injection of the catalyst suspended in an inert hydrocarbon solvent, into the polymerization zone, the zirconium may have a reduced valency and be at least in part in the Zr(III) valence state although some Zr(II) and Zr(IV) may also be present.

The polymerization process is carried out in an inert, substantially anhydrous hydrocarbon medium. The temperature employed may range from about 20° C. to 300° C., depending on the monomer or monomers to be polymerized and upon whether a slurry or a solution polymerization process is to be used. In the case of the polymerization of ethylene, either homopolymerization or copolymerization with other olefins, the preferred temperature is in the range of 130°–270° C. where a single phase, solution polymerization process occurs at maximum rates and high efficiency (yield of polymer per unit of zirconium catalyst). Propylene is preferably polymerized at lower temperatures in the range of 50° to 150° C. although higher temperatures can be employed.

The pressure employed is not critical so long as it is sufficient, at the temperature chosen, to prevent boiling of the hydrocarbon solvent and maintain the monomers employed in solution in the solvent. Thus the pressure may range from atmospheric to 1,000 atm. and above at the highest temperatures of operation of the process.

The process employed for the preparation of the catalyst is a critical aspect of the invention. In order to achieve optimum activity it is preferred that an alumina having a surface area of 10 to 500 m$^2$/g, free from absorbed water but containing hydroxyl groups generally randomly distributed on its surfaces be employed. Preferably this alumina support is most readily produced by activation of fumed alumina (a product obtained by burning aluminum chloride in the presence of water vapor) by heating in a stream of dry N$_2$ at temperatures in the range of 900°–1100° C. for a period in the range of 1 to 10 hours. This treatment not only removes water and residual chloride from the fumed alumina but alters the morphology of the crystalline alumina from predominantly gamma-alumina to a particular mixture of the gamma-, delta-, theta-, and alpha forms. The resultant mixture of crystalline forms is essential for obtaining, in the subsequent reactions with tetra(neophyl) zirconium, the unique chemical composition of the zirconium neophyl aluminate necessary to produce the optimum catalyst which exhibits the unexpected and surprising activity and efficiency characteristic of the preferred polymerization process of this invention.

The fumed alumina, activated as described above, is then subjected to partial hydration by contact with an atmosphere comprising some water vapor until a minor proportion of water has reacted with the alumina surface, conveniently about 3% to 5% by weight water of hydration. This rehydrated alumina may then be partially dehydrated by heating at a temperature in the range of 300° to 500° C. for from 1 to 10 hours, the time requred being in the lower portion of the range at the higher temperatures in the range of temperatures. The final product contains from 0.5% to 1.5% by weight water as HO groups distributed on the surfaces of the alumina. This second heat treatment not only assures that no merely absorbed molecular H$_2$O remains on the surfaces of the alumina but also eliminates any large clusters of HO-groups on the surfaces leaving randomly distributed on the Al$_2$O$_3$ surfaces pairs and relatively isolated HO-groups as reactions sites. The high temperature activation removes essentially all H$_2$O and HO-groups from the alumina, decreases the amount of residual chloride from an initial 0.7% to 0.2% by weight and, very importantly, converts a portion of the original gamma crystalline Al$_2$O$_3$ to the more active delta and theta forms. Partial rehydration with water vapor in a moist atmosphere replaces hydroxyl groups on the Al$_2$O$_3$ surfaces.

The final drying at about 400° C. reduces the concentration of HO-groups on the surfaces of the Al$_2$O$_3$ to an optimum value in the range of o.5 to 1.5% by weight water, thus providing isolated single and pairs of HO-groups on the alumina surfaces, making these surfaces most suitable for reaction with tetra(neophyl) zirconium in solution.

The preferred catalyst is next prepared by mixing together a suspension of the activated, hhydroxylated alumina in anhydrous mineral oil with a solution in hydrocarbon solvent of tetra(neophyl) zirconium. In general, the proportion of tetra(neophyl) zirconium emploued is at least 0.05 millimoles per gram of Al$_2$O$_3$, preferably 0.15 to 0.35 millimoles per gram Al$_2$O$_3$, or other metal oxide. Larger proportions are operably but provide no advantage since they provide no enhancement of catalyst activity.

The reaction between tetra(neophyl) zirconium and hydroxylated alumina can be conducted at temperatures in the range of 0° to 100°C., depending on the time allowed. Upon mixing the suspension of alumina with the solution of tetra(neophyl) zirconium, a reaction occurs between the HO-groups on the surfaces whereby Zr-O-Al chemical bonds are formed with the elimination of approximately 2.5 of the 4 hydrocabyl radicals originally bonded to the zirconium. The reaction may be approximately described by the equations (A) and (B):

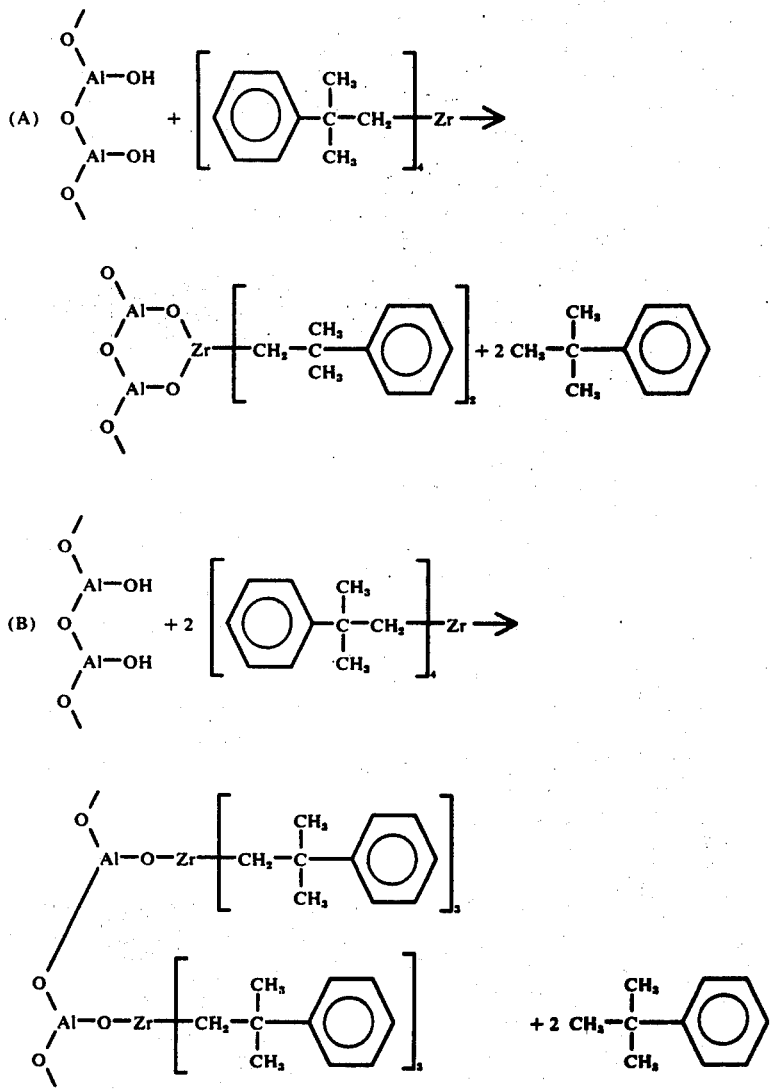

There then follows upon aging, particularly at 50° C. and above, a partial decomposition to form the active catalyst in which zirconium is at least in part in lower valence states. This is shown by (C):

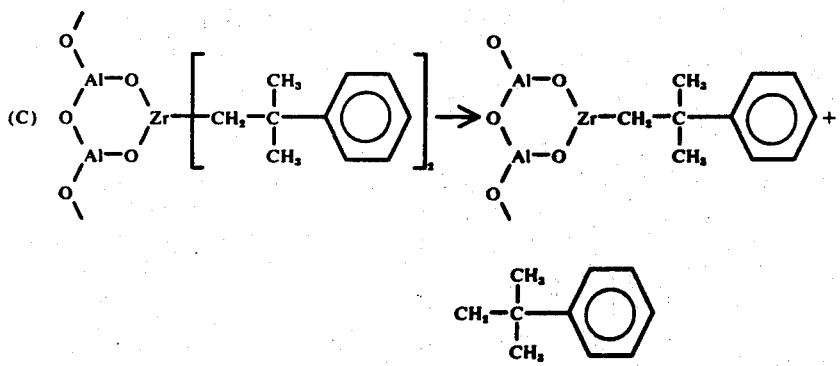

The neophyl radicals eliminated may either be converted to t-butyl benzene by picking up a proton from the solvent, or may couple. Some zirconium may similarly be reduced to Zr(II) at active polymerization sites, particularly in the presence of olefin monomers.

In the ethylene polymerization process of this invention when conducted in contrinuous manner in a stirred autoclave, the yields obtained have been in excess of 10,000 parts of polyethylene per part of zirconium when using the preferred neophyl zirconium aluminate bonded onto alumina catalyst. Inherently, batch processes are less efficient but yields in the range of 700–1000 g. polyethylene per millimole od zirconium pwe hour are readily obtainable as compared with only 50 to 100 g. polyethylene per millimole Zr obtained in a process of the prior art where there is used as catalyst the reaction product of tetra(benzyl) zirconium with hydrated $Al_2O_3$.

In the peferred continuous process, the catalyst suspension and the ethylene dissolved in an aliphatic or cycloaliphatic hydrocarbon are each fed continuously to the stirred polymerization zone, the molar ratio of ethylene fed to zirconium being maintained in the range of 35,000–400,000 to one.

The polyolefins obtained by the process of this invention are linear, head-to-tail polymers of high molecular weight. In the case of ethylene homopolymerizations, the resultant linear polyethylene has a crystalline melting point in the range of 133°–138° C., an annealed density in the range of 0.96 to 0.97 g./cm$^3$. If desired, ethylene polymers of lower density (0.90–0.96 g/cm$^3$) can be obtained by copolymerization of ethylene with minor proportions (0.1 to 15 mole%) of higher $\alpha$-olefins (preferably $C_4$ to $C_{10}$) to provide copolymers containing 0.1 to 12 weight % copolymerized higher olefin using the process and catalyst of this invention. Such copolymers contain randomly-distributed side chains of controlled length which impede somewhat the development of crystallinity in the solid polymers which are, as a result, polymers of increased troughness and stress-crack resistance. As is well know, all of the ethylene polymers find commercial use as self-supporting films, wire-coatings, pipe, and molded articles of commerce. If desired, they can be filled with glass or other stiff fibers, clays and the like to produce hard, stiff moldings.

The homopolymerization of propylene using the catalysts of this invention in the process of this invention can be directed, by control of process conditions, to yield highly stereoregular, head-to-tail crystalline polypropylene of high molecular weight insoluble in hydrocarbons at ambient temperatures and sparingly soluble even at temperatures above 100° C. and having a crystalline melting point in the range of 162°–170° C., as determined by either differential thermal analysis or hot-stage microscope using polarized light, as well as high molecular weight, linear, head-to-tail polypropylene polypropylene is amorphous, due to atactic steric structure, and soluble in hydrocarbons even at room temperature. The crystalline polypropylene has come to be termed, following the suggestion of Giulio Natta, polypropylene exhibiting "isotactic" structure due to the presence of long segments in the macromolecules in which the groups attached to successive asymmetric carbon atoms along the chains have the same configuration. As is well know, crystalline polypropylene finds many commercial uses, particularly as textile fibers, in both woven and non-woven textiles and as films, strappings, coatings and molded articles of commerce. Amorphous polypropylene is useful in blends with crystalline polyolefins to provide toughness, and in adhesive compositions and rubbers.

The catalysts and processes of this invention can be used to produce amorphous ethylene/propylene rubbers where from about 30% to about 72% by weight (preferably about 50% by weight) of ethylene and, correspondingly, 70% to 28% of propylene are combined in the macromolecules by copolymerization, under constant environment conditions, of ethylene and propylene. Due to the higher reactivity of ethylene in the polymerization reaction, a higher proportion of propylene should be used in the monomer feed fed to the polymerization zone than it is desired to incorporate in the copolymer macromolecules. If desired to provide ready sites for subsequent traditional chemical vulcanizations (cross-linking), minor proportions of unconjugated dienes (e.g. 1,4-hexadiene, 2-methyl-1,5-hexadiene, etc. ) may be included in the copolymers by including minor proportions of these diene monomers in the mixture of monomers fed to the polymerization zone in the process. Rubbers can also be obtained by the homopolymerization of conjugated diolefins such as butadiene or isoprene using the catalysts and process of this invention. The properties and utilities of these synthetic rubbers are well known in the rubber industry.

Because the process of this invention uses such an active and efficient catalyst system, the very low level of catalyst residues in the polyolefin products produce no adverse effects on the properties of these polymers. Therefore, the polymers are used as formed without the necessity of the expensive and complex catalyst removal procedures customarily employed in connection with prior art commerical practice.

The following examples are provided to illustrate the invention and to provide comparative examples closer to the more relevant prior art. However, the invention is not to be considered as limited to the particular examples provided but rather is of the scope hereinabove described and hereinafter claimed.

EXAMPLE 1

Preparation of Tetra(Neophyl)Zirconium

Magnesium turnings (48.6 g., 2.0 moles) were charged into a 2-liter, 3necked glass flask fitted with a stirrer, $N_2$ inlet, $N_2$exit connected to a mineral oil bubbler, and 500 cc. dropping funnel. The flask was swept with $N_2$ overnight to remove air and moisture. Then 160 cc. of dry, deoxygenated diethyl ether was added. A crystal of iodine was added to activate the Mg surface, and then 118 g. (0.7 moles) of neophyl chloride dissolved in 160 cc. of dry toluene was added dropwise. The reaction mixture was continuously stirred and maintained at 30°–35° C. until all of the neophyl chloride had been added. The reaction mixture turned brown during this period. After 1 hour a 5cc. aliquot of the supernatent solution was removed from the reaction mixture, neutralized with 20 cc. of 0.1 M aqueous HCl and back-titrated to a pink phenolphthalein end point with 5 cc. of 0.2 M aqueous NaOH. The concentration of the Grignard reagent was therefore fround to be 2 molar.

The Grignard reagent was transferrd to a 2-liter flask swept with a stream of dry $N_2$. The unreacted Mg was washed with 400 cc. of dry toluene and the washing added to the Grignard solution. The Grignard solution (neophyl magnesium chloride) was cooled to −10° C. and then 40 g. of 97% $ZrCl_4$ (0.166 moles) was added through a solids addition tube. The slurry was stirred for 1 hour and warmed to 50° C., then transferred to an inert atmosphere box and filtered through a 1-inch bed of dried "Celite" (diatomaceous earth). The filtrate was concentrated by evaporation. Crystals of solid tetra(neophyl) zirconium formed upon cooling. The yield of this product was about 70 g. The crystals were purified by recrystallization from n-hexane. The purified tetra(neophyl) zirconium product was found to melt at 67–68° C. by observation on a Fisher-Johns hot-stage and 69° C. by DSC melting point determination in $N_2$. Elemental analysis of this product gave C = 75.85%, H = 8.20%; theory for tetra(neophyl) zirconium, C = 76.99%, H = 8.40%.

EXAMPLE 2.

Preparation of a Neophyl Zirconium Aluminate on Alumina Catalyst a. Activation of Alumina 111.2 g. of a commercial grade of fumed alumina having a surface area of 100 $m^2/g$ was charged to a vertical quartz reactor and dried at 1000° C. in a stream of flowing $N_2$ for 6 hours. The dry $Al_2O_3$ was partially rehydrated by contact with a 50% relative humidity atmosphere at 73° F. for 16 hours and then redried to optimum HO-group content by heating at 400° C. for 4 hours in a stream of flowing $N_2$.

The resultant activated alumina was suspended under a $N_2$ atmosphere in 1900 cc. of mineral oil containing 100 cc. of petroleum jelly and stored under $N_2$ until used. A sample of the slurry was ashed and found to contain 0.048 g. alumina per cubic centimeter.

b. Catalyst Preparation

Ten cubic centimeters of a solution containing 0.074 g. of the tetra(neophyl) zirconium of Example 1 dissolved in decahydronaphthalene ("Decalin") was added to 10cc. of the suspension of alumina in mineral oil with continuous stirring and this mixture was allowed to react at 25° C. for 21 hours to provide a suspension of neophyl zirconium aluminate bonded onto alumina in mineral oil which was subsequently used to polymerize ethylene. The zirconium in this product was in a reduced state.

EXAMPLE 3.

Polymerizatin of Ethylene at 150° C. Using Neophyl Zirconium Aluminate on Alumina as Catalyst A 350 cc. crown-capped bottle was charged with 340 cc. of dry, deoxygenated decahydronaphthalene solvent, heated to 150° C. and the solvent saturated with ethylene charged at 40 psi. 3.0 cc. of the suspension of neophyl zirconium aluminate bonded onto alumina in mineral oil prepared in Example 2 was then charged into the solution of ethylene. After 3 mintues, the polymerization was terminated by the addition of 2 cc. of isopropanol which reacts to destroy the activity of the catalyst. The reaction mixture was cooled which caused the polyethylene to precipitate. The solid polyethylene was isolated by filtration, washed with cyclohexane and methanol and dried in a vacuum oven at 80° C. for 16 hours. The yield of solid, dry polyethylene was 0.7 g. Based on this yield, the rate of polymerization was calculated to have been 780 g/millimole Zr/hr. The solid, linear polyethylene was white and had a crystalline melting point of 133° C., as determined by DSC technique, and was of high molecular weight.

EXAMPLE 4.

Polymerization of Ethylene at 80° C. Using Neophyl Zirconium Aluminate on Alumina as Catalyst A 350 cc. crown-capped Pyrex bottle containing 200 cc. of dry, deoxygenated toluene maintained at 80° C. was saturated with ethylene at 40 psi. There was then charged into this solution of ethylene 3.0 cc. of the suspension in mineral oil of neophyl zirconium aluminate on alumina, prepared in Example 2. Polymerization commenced at once as shown by precipitation of polymer. Additional ethylene was charged into the reactor to maintain the pressure at 40 psi. After 1 hour at 80° C., the polymerization was terminated by the addition of 2 cc. of isopropanol, and the granular polyethylene was recovered by filtration and dried in a vacuum oven at 80° C. for 16 hours. The weight of dry, solid linear polyethylene recovered was 1.3 g. The polyethylene had a crystalline melting point of 135° C. as determined by DSC techniques and was of high molecular weight.

EXAMPLE 5.

Polymerization of Ethylene at 80° C. Using Tetra(neophyl)Zirconium as Catalyst

A 350 cc. crown-capped bottle was charged with 200 cc. of dry, deoxygenated toluene and saturated at 80° C. with ethylene. A 0.1 M solution in benzene of the tetra(neophyl) zirconium of Example 1 as prepared, and 1 cc. of this solution was charged into the toluene solution of ethylene. Polymerization commenced immediately as shown by the precipitation of polymer. Additional ethylene was charged to maintain the pressure at 40 psi. After 1 hour at 80° C., polymerization was terminated by addition of 2 cc. of isopropanol. The solid polyethylene was isolated by filtration and dried in a vacuum oven for 16 hours at 80° C. The weight of the recovered, dry, solid white polyethylene was 0.934 g. The polyethylene had a crystalline melting point of 135.8° C., as determined by DSC measurement. Based on the yield of polymer, the rate of polymerization was calculated to have been 9.34 g/millimole Zr/hr. The polyethylene was of high molecular weight.

EXAMPLE 6.

Comparative Activity of Neophyl Zirconium Aluminate and Benzyl Zirconium Aluminate on Alumina as Catalysts for the Polymerization of Ethylene in a Continuous Process a. Polymerization of ethylene using neophyl zirconium aluminate on alumina as catalyst A 0.000625 M solution in n-hexane of the tetra(neophyl) zirconium of Example 1 was prepared. A suspension of an active supported catalyst comprising neophyl zirconium aluminate on alumina was continuously prepared by feeding the 0.000625 M solution of tetra(neophyl) zirconium at a rate of 200 cc./hr. and a suspension of activated alumina, prepared as in Example 2(a), at a rate of 0.5 g. $Al_2O_3$/hr. into a stainless steel, stirred autoclave of 975 cc. capacity where it was diluted with 1400 cc. of hexane maintained at 50° C. After a hold-up time of approximately 40 minutes, to allow for the reactions between tetra(neophyl) zirconium and the activated alumina to produce neophyl zirconium aluminate, the catalyst suspension was continuously fed to a 265 cc. stainless steel autoclave, at the same rate, and there diluted with 800 cc./hr. of n-hexane. After a hold-up of 6 minutes in the autoclave the diluted catalyst suspension then was continuously fed to a 253 cc. stainless steel, agitated polymerization vessel maintained at 2250 psi and 250° C. where it was contacted with ethylene fed, as a 7% weight solution in n-hexane, at 200 g. ethylene/hr. The concentration of the catalyst in the reactor with respect to zirconium was 2.0 × 10$^{-5}$ molar. In order to control and limit molecular weight of the polyethylene, H$_2$ was also fed to the polymerization vessel at a rate of 100 millimoles/hr. as a 0.0825 M solution in n-hexane. The hold-up time in the polymerization vessel was maintained at approximately 2.56 minutes by continuously withdrawing the polymerization mixture to a deactivation chamber where the catalyst was deactivated to terminate the polymerization by addition of a 0.0033 M solution of isopropanol in n-hexane at a rate of 600 cc./hr. to the reaction mixture containing dissolved polyethylene.

The solution of polyethylene was continuously discharged through an automatic, controlled pressure-reducing valve into a product receiver maintained at 50° C. where the solid polyethylene was recovered from the polymerization medium by filtration, and the polyethylene, wet with n-hexane, was chopped in a blender, washed with n-hexane and dried in a vacuum oven at 80° C. for 16 hours.

The rate of polyethylene production during steady-state operation over a period of several hours was 177 g./hr. (88.5% conversion of the ethylene fed to the polymerizer). The yield of polyethylene was 1415 kg/mole of zirconium. The dried polyethylene had a melt flow, as determined by ASTM Method 1238-65T, Condition E, of 2.8 decigrams/min. The density of the polyethylene produced, as determined by ASTM D792-64T (method corrected to 23° C.) was found to be 0.960 g/cc. Thus the polyethylene produced was a highly linear, crystalline polyethylene of high molecular weight suitable for use in production of films and injection-molded articles.

b. Polymerization of ethylene using benzyl zirconium aluminate as a catalyst

The foregoing experiment (Example 6a) was repeated using as a catalyst the reaction production of the activated alumina and tetra(benzyl) zirconium except that the concentration of zirconium catalyst was increased slightly to 2.14 × 10$^{-5}$ molar in the polymerization autoclave. In this instance the rate of polyethylene formation was 167 g./hr. (83.8% conversion of the ethylene fed).

An analysis of the reactions based on the change in activity (a) as shown by $$a = \frac{1}{\tau}\left(\frac{Q}{1-Q}\right)$$

where
$\tau$ = hold-up time in the polymerizer
$q$ = ethylene conversion reveals $a$'s of 3.029 min$^{-1}$ for the neophyl zirconium aluminate catalyst vs. only 2.017 min$^{-1}$ for the benzyl zirconium aluminate catalyst. Thus even though the concentration of neophyl zirconium aluminate catalyst in the polymerizer was less (2.0 × 10$^{-5}$ molar) than benzyl zirconium aluminate catalyst (2.14 × 10$^{-5}$ molar) the activity of the neophyl zirconium aluminate was 1.5 times that of benzyl zirconium aluminate.

EXAMPLE 7.

Polymerization of Propylene Using Neophyl Zirconium Aluminate on Alumina As Catalyst Into a 1-liter, stirred, nitrogen-filled autoclave was charged 600 ml of cyclohexane purified by purging with nitrogen followed by passing it through a bed of acid alumina under nitrogen. As the autoclave was kept blanketed with nitrogen 0.2 millimoles of neophyl zirconium aluminate supported on 1 gram of fumed alumina, prepared as in Example 2, was injected by syringe as a slurry in 20 ml. of cyclohexane. Propylene was pressured in to 20 psi as the system was stirred at 500 rpm. The temperature and propylene pressure was raised to 50°/60 psi and maintained at this for 4 hours. The 10 grams of polypropylene obtained was in the form of a gel, which was evaporated to give a tough, flexible sheet. The inherent viscosity of this polymer was 12.5 dl/100 as measured at 0.1% concentration in decalin at 130°C. Thirty-five percent of the polymer was insoluble in boiling heptane. The insoluble polypropylene was highly crystalline and exhibited the isotactic structure. A very tough, rubbery film 5 mils thick was obtained by compression molding 0.5 g. of the total polymer at 230° C., 3000 lbs. ram pressure.

Example 8

Polymerization of Ethylene with a Neophyl Zirconium Silicate on Silica Catalyst 20 g. of a commercially available fumed silica having a surface area of 225 m$^2$/g was charged to a vertical glass reactor and dried at 200° C. in a stream of flowing nitrogen for 4 hours. One gram of the dried silica was suspended in 38.5 cubic centimeters of decahydronaphthalene and 1.5 cc of 0.2M tetra(neophyl) zirconium in benzene was added. After 40 minutes the supernatent liquid above the catalyst was analyzed by gas chromatography. A material balance showed approximately 2.1 neophyl groups were displaced from each mole of tetra(neophyl) zirconium during formation of the neophyl zirconium silicate on silica catalyst.

The polymerization of ethylene was brought about by charging a crown capped bottle containing 340 cc of decahydronaphthalene saturated with ethylene at 150° C and 40 psi with 4 cubic centimeters of the neophyl zirconium silicate on silica catalyst (0.1 g silica, 0.03 millimole Zr). After 3 minutes the polymerization was stopped by addition of 2 cubic cnetimeters of isopropanol. The solution was cooled and the precipitated polymer separated by filtration, washed with cyclohexane and methanol, and dried in a vacuum oven for 16 hrs. at 80° C. The product recovered, including catalyst residue, weighed 0.345 g which is equivalent to 0.245 g of polyethylene. Based on this yield the rate of polymerization was calculated to have been 163 g/millimole Zr/hr as contrasted with the 780 g/millimole Zr/hr achieved in Example 3 by use of the preferred catalyst of this invention.

EXAMPLE 9

Copolymerization of Ethylene and Propylene with a Neophyl Zirconium Aluminate on Alumina Catalyst to form a Crystalline Copolymer

80 cubic centimeters of deoxygenated hexane in an agitated vessel was saturated at 25° C. with propylene at 20 psi. The pressure was raised to 40 psi with ethylene and the copolymerization brought about by the addition of 10 cubic centimeters of a neophyl zirconium aluminate catalyst slurry prepared by reaction of 10 g of alumina activated as in Example 1 and 2.0 millimoles of tetra(neophyl) zirconium in 210 cubic centimeters of deoxygenated hexane. After 20 minutes at 25° C the polymerization was stopped by venting the unreacted olefins. The polymer was separated by filtration washed with methanol and dried at 80° C. for 16 hrs. The product recovered weighed 6.44 g. This copolymer had a crystalline melting point of 122.5° C, by DSC techniques and was found to contain 10.1 weight % copolymerized propylene by infrared analysis.

EXAMPLE 10

Copolymerization of Ethylene and Propylene With a Neophyl Zirconium Aluminate on Alumina Catalyst to Produce an Amorphous Copolymer 2 grams of alumina activated as in Example 1 was suspended in 40 cubic centimeters of hexane and 2 cubic centimeters of a 0.2 molar solution of tetra(neophyl) zirconium in benzene added. After 1 hr. a portion of the slurry was transferred to a vial and the hexane evaporated under vacuum leaving 1.06 g of catalyst. The vial was sealed and placed in a stanless steel reactor with two stainless steel balls. The reactor was sealed and charged with 50 g of propylene, warmed to 25°C. and ethylene added until the pressure in the reactor reached 500 psi. The catalyst ampoule was broken and the polymerization allowed to proceed for 1 hr. The amorphous copolymer, isolated as a rubbery ball, was separated from the glass and dried to yield 29 g of copolymer having a copolymerized propylene content of 28.3 weight percent, as determined by infrared analysis.

EXAMPLE 11

Polymerization of 1,3-Butadiene with a Neophyl Zirconium Aluminate on Alumina Catalyst A 1 liter agitated flask swept with nitrogen was charged with 500 cubic centimeters of deoxygenated toluene, heated to 50° C. and saturated with 1,3-butadiene at 2 psi.

Neophyl zirconium aluminate on alumina catalyst in hexane, equivalent to 0.38 g. of catalyst (0.076 millimoles Zr), was added and the polymerization continued for 1 hr. The product which formed was separated by filtration, chopped in a blender and dried in a vacuum oven at 80° C. for 16 hrs. The dried product weighted 1.13 g. which is equivalent to 0.75 g. of polybutadiene. Based on this yield the rate of polymerization was calculated to be 9.9 g./millimoles Zr/hr. Infrared analysis showed the structure of the polymer to be of the 1,4-trans-type.

EXAMPLE 12

Polymerization of Propylene With a Neophyl Zirconium Aluminate on Alumina Catalyst 1 gram of alumina activated as in Example 1 was suspended in 40 cubic centimeters of dry hexane in a stirred flask under nitrogen. 5 cubic centimeters of 0.1 molar tetra(neophyl) zirconium was charge to the flask. After 16 hrs. the neophyl zirconium aluminate catalyst was transferred to an ampoule and the hexane evaporated under high vacuum. The ampoule was sealed and placed in a stainless steel reactor with two stainless steel balls. The reactor was swept with nitrogen to exclude all air, sealed, evacuated, cooled and 75 g of propylene charged. The reactor was warmed to 50° C. and the ampoule broken by shaking the reactor. After 1 hour the polymer was isolated, separated from the glass and dried to yield 26 g. of polypropylene having a melting point of 158° C. and a crystallization point of 110° C. by DSC. The polypropylene had an inherent viscosity in decahydronaphthalene at 130° C. (0.1% solution) of 9.64. Extraction of the polypropylene with boiling hexane for 4 hrs. removed 3% of the polymer indicating the remainder to be substantially high molecular weight polypropylene of isotactic structure. The hexane insoluble fraction was further extracted with boiling toluene. The swollen toluene insoluble residue, after drying, had a melting point of 162.5° C. by D.S.C., and amounted to 90% of the original crude product. The insolubiltity in toluene at the boiling point indicates that this crystalline polypropylene comprises macromolecules having substantially completely the isotactic structure.

EXAMPLE 13

Terpolymerization of Ethylene, Propylene and 1,4-Hexadiene with Neophyl Zirconium Aluminate on Alumina Catalyst 4 Grams of alumina activated as in Example 1 was suspended in 80 cubic centimeters of hexane and reacted with 12 cubic centimeters of a 0.1 molar solution of tetra(neophyl) zirconium in benzene. A portion of the slurry was transferred to a glass ampoule and the liquid evaporated and the catalyst dried under high vacuum. The dry catalyst in the ampoule weighed 1.277 g. The ampoule was placed in a stainless steel reactor with 2 stainless steel balls. The reactor was closed and charged with 50 cubic centimeters of 1,4-hexadiene and 50 cubic centimeters of n-hexane. The reactor was cooled, charged with 50 grams of propylene, warmed to 100° C. and pressured to 800 psi with ethylene. The catalyst ampoule was broken and the terpolymerization allowed to proceed for 1 hour. The polymer isolated as a crumb was separated from glass and dried to yield 9 g of terpolymer. A melt pressed film of the terpolymer was analyzed by infrared analysis and found to contain 5.5 methyl groups/100 carbons and 8.3 trans-olefin groups/2000 carbons which is equivalent to 15.6% propylene and 2.43% hexadiene by weight.

EXAMPLE 14

Terpolymerization of Ethylene, Propylene and 5-Ethylidene Norbornene with Neophyl Zirconium Aluminate on Alumina Catalyst 0.7353 Gram of dry neophyl zirconium aluminate on alumina catalyst prepared as in Example 13 was sealed in a glass ampoule. The catalyst ampoule was placed in a stainless steel reactor with 2 stainless steel balls. The reactor was closed, charged with 20 cubic centimeters of 5-ethylidene norbornene, cooled, and charged with 75 g of propylene. After warming to 100° C. the reactor was charged with 700 psi ethylene and the catalyst ampoule broken. After 1 hour the polymer was isolated, separated from glass and dried in a vacuum oven at 80° C. for 16 hours. A melt-pressed film of the terpolymer was analyzed by infrared analysis and found to contain 12 methyl groups/100 carbons and 4.6 trans-olefinic groups/100 carbons, which is equivalent to a composition of 32 weight % propylene and 1.97 weight % ethylidene norbornene in the terpolymer.

EXAMPLE 15

Copolymerization of Ethylene and 1-Octene Using Neophyl Zirconium Aluminate on Alumina Catalyst 1.12 Gram of dry neophyl zirconium aluminate catalyst prepared as in Example 13 except having a zirconium content of 0.2 millimoles per gram of alumina was sealed in an ampoule and charged to a stainless steel reactor containing 2 stainless steel balls. The reactor was freed of air and charged with 10 cubic centimeters of 1-octene, warmed to 100° C., and pressured with 700 psi of ethylene. The catalyst vial was broken and the copolymerization allowed to proceed for 1 hour. The product was isolated, separated from glass and dried. The dry copolymer weighted 3.3 g and had a melting point of 120° C. as determined on a differential scanning calorimeter (Du Pont Model 900).

Since the catalysts of this invention are subject to deactivation by $O_2$, $H_2O$, $CO_2$ other reactive substances, in all of the examples precautions were taken to maintain the equipment clean and dry and free from atmospheric contact, and the solvents, $H_2$ and monomer were freed from traces of moisture or oxygen by the use of conventional desiccating agents and alkali metals.

As shown by the examples, the preferred catalyst of this invention has a remarkably high activity as an olefin polymerization catalyst compared to coordination catalysts previously known. It has the further very significant advantage that, due to its high activity, the low concentration and the innocuous character of the catalyst residues, which are white, free from corrosive halogens and non-toxic, it is not necessary to remove the low level of catalyst residues from the polyolefins produced. This eliminates the expensive, time-consuming catalyst-removal process steps characteristic of previously-known commercial processes for the preparation of polyolefins using coordination catalysts.

The olefin polymers produced by the process of this invention are regular, linear head-to-tail polymers of high molecular weight useful for subsequent fabrication by conventional equipment into tough colorless films, fibers, molded articles, pipe and wire coatings.

ANALYTICAL METHODS a. The melting points of the polyolefins prepared were accurately determined by differential thermal analysis according to the general method described in the chapter "Application of Differential Thermal Analysis to High Polymers," Organic Anslysis Volume IV, page 361, Interscience Publishers, Inc. (1960). Using a differential thermal analyzer, e.g., a Du Pont Model 900 DTA, fitted with a differential scanning calorimeter (DSC) cell adjusted to a heating rate of 5° C. per minute using an empty aluminum pan as a reference, a sample of the polymer was heated in an aluminum pan to 20° C. above its melting point. The sample was cooled approximately 15 minutes until it reached a temperature of about 50° C. and then reheated, again at 5° C. per minute, and the melting point observed. This procedure gives comparable melting points for polyolefins to those obtained by visual observation using a hot-stage microscope equipped with crossed polarizers in accord with the ASTM procedure Designation D2117-64 for the determination of the melting point of semicrystalline polymers.

b. One method for molecular weight determination is the measurement of inherent viscosity of the polymer in solution. The measurement of inherent viscosity bears a direct relationship to the number average molecular weight for each class of polyolefin and it was used in the above examples to characterize the polypropylene products of the examples. The inherent viscosity ($\eta_i$) of the polypropylene was measured by dissolving 0.05 g. of the polyolefin in 50 milliliters of decahydronaphthalene at 170° C. The solution was filtered and transferred to an Ostwald viscometer and the viscosity of the polymer solution and of the decahydronaphthalene solvent measured at 130° C. by noting the time required to pass the same volume of each material through the viscometer.

The inherent viscosity ($\eta_i$) was then calculated by using the following formula:

$$\eta_i = \frac{2.303 \log [\text{flow time for solution/flow time for solvent}]}{\text{gm. of polymer in 100 ml. of solvent.}}$$

The inherent viscosity may be correlated with the number average molecular weight of the linear polyolefin, e.g., an inherent viscosity of 1.0 corresponds to a number average molecular weight of 180,000, an $\eta_i$ of 5 corresponds to 750,000 and $\eta_i$ of 10 corresponds to 1,800,000 for the polypropylene polymers disclosed herein.

c. The weight average molecular weight of the polyolefin products herein may be measured by the classical methods of light scattering. However, in the case of the linear polyethylene products of the examples, the weight average molecular weights of the products herein were determined from a previously-established correlation between melt flow (ASTM 1238-65T Condition E) and weight average molecular weight as determined by light scattering, e.g., a melt flow of 1 corresponds to a weight average molecular weight ($\overline{M}_w$) of 140,000 and a melt flow of 3.5 to $\overline{M}_w = 100,000$.

d. The characterization of tetra(neophyl) zirconium by nuclear magnetic resonance spectroscopy was carried out according to the general proceduce described in "Interpretation of NMR Spectra" by R. H. Bible, Plenum Press, 1965; Appendix, page 119. The tetra(neophyl) zirconium (0.02 g.) was dissolved in 0.2 cc of deutrobenzcne (99.8%) in a 5 mm. O.D. × 5 inch glass NMR tube. The spectrum was determined at 42° C.

I claim:
1. Tetra(neophyl)zirconium.

\* \* \* \* \*